United States Patent [19]
Kondo et al.

[11] 3,988,380
[45] Oct. 26, 1976

[54] PROCESS FOR PREPARING 1,2-DISUBSTITUTED-TRANS-OLEFINS

[75] Inventors: Kiyosi Kondo; Akira Negishi, both of Yamato; Daiei Tunemoto, Sagamihara, all of Japan

[73] Assignee: Sagami Chemical Research Center, Tokyo, Japan

[22] Filed: Dec. 3, 1974

[21] Appl. No.: 529,083

[30] Foreign Application Priority Data
Dec. 7, 1973  Japan............................. 48-136070
Dec. 7, 1973  Japan............................. 48-136071

[52] U.S. Cl. .................. 260/632 R; 260/345.9; 260/632 B; 260/682
[51] Int. Cl.² .................................... C07C 29/10
[58] Field of Search............ 260/345.9, 682, 632 R, 260/632 B

[56] References Cited
UNITED STATES PATENTS
3,773,789  11/1973  Fried.............................. 260/345.9
3,855,247  12/1974  Fried.............................. 260/345.9
3,879,449  4/1975   Anderson et al. ............... 260/345.9
3,880,884  4/1975   Fried.............................. 260/345.9

OTHER PUBLICATIONS

Meyers et al., Tetrahedron, Pergamon Press, vol. 27, pp. 5979–5985 (1971).

*Primary Examiner*—James O. Thomas, Jr.
*Assistant Examiner*—G. Breitenstein
*Attorney, Agent, or Firm*—Sherman & Shalloway

[57]  ABSTRACT

A new process for preparing 1,2-disubstituted-trans-olefins selectively by reacting specific 2-alkenyl phosphonic acid derivatives with metal hydrides, and a new process for producing the specific 2-alkenylphosphonic acid derivatives. The 1,2-disubstituted-trans-olefins are useful as precursors for synthesis of insect pheromones.

11 Claims, No Drawings

PROCESS FOR PREPARING 1,2-DISUBSTITUTED-TRANS-OLEFINS

This invention relates to a new process for preparing 1,2-disubstituted-trans-oleins, and to a process for preparing 2-alkenyl phosphonic acid derivatives used as starting materials in the above process.

According to this invention, 1,2-disubstituted olefins in the trans form expressed by formula (I)

wherein $R^1$ and $R^2$, independently from each other, represent a hydrogen atom or an alkyl or alkenyl group with the proviso that $R^1$ and $R^2$ do not represent hydrogen atoms at the same time, and $R^3$ represents an unsubstituted or substituted alkyl group, an unsubstituted or substituted alkenyl group, or an aralkyl group, are selectively prepared.

The 1,2-disubstituted-trans-olefins of formula (I) have a main skeleton structure of insect pheromones, and therefore, are useful as precursors for synthesis of insect pheromones. The insect pheromones are substances which are produced within the bodies of insects and secreted out of the bodies, and thereby strongly influence the behavior of other individuals of the same species. Examples of the insect pheromones are arylgyroploce leucotreta (Tortricidae)

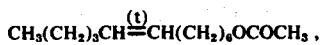

and sparganotis sulfureana (do.)

both as sex attractants.

Some of these insect pheromones have previously been synthesized chemically by a number of complicated steps using dichlorotetrahydropyrane as a starting material [J. Medical Chem., vol. 10, 533, (1967)].

A method was previously known for synthesizing olefins by reacting phosphonic acid ester derivatives with aldehydes or ketones in the presence of a base, as a modified Wittig reaction. This reaction only affords a mixture of trans- and cis-olefins. With a view to improving such a Wittig reaction, M. Schlosser et al. recently suggested a process for selectively preparing trans-olefins from triphenyl alkyl phosphonium salts [Chem. Ber., 103, 2814, (1970)]. This process, however, suffers from some difficulties. For example, the starting material is relatively expensive, and the operation of reaction is complicated because the reaction intermediate must be treated with a basic substance. In addition, the reaction conditions should be very strictly set up. There was also known a method involving the half-reduction of an acetylene compound, for example, a dialkyl acetylene, with sodium in liquid ammonia [R. A. Benkeser, J. Am. Chem. Soc., 77, 3378 (1955)]. With this method, however, it is extremely difficult to obtain trans-olefins selectively. According to this invention 1,2-disubstituted-olefins of formula (I) having trans form can be obtained from a relatively cheap material selectively, easily, and economically advantageously. The process for preparing 1,2-disubstituted-trans-olefins of formula (I) in accordance with this invention comprises reacting 2-alkenyl phosphonic acid derivatives of formula (II)

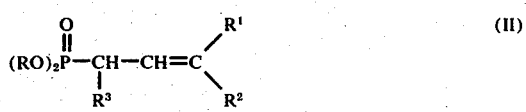

with metal hydrides. In the above formula, R is an alkyl group, and $R^1$, $R^2$ and $R^3$ are as defined above.

Irrespective of whether the starting 2-alkenyl phosphonic acid derivative is in the trans form or in the cis form, the process of this invention affords selectively the trans form of 1,2-disubstituted-olefins as a result of the reductive liberation of the phosphonic acid ester moiety involving the rearrangement of the double bond. For example, the reaction can be schematically shown as follows:

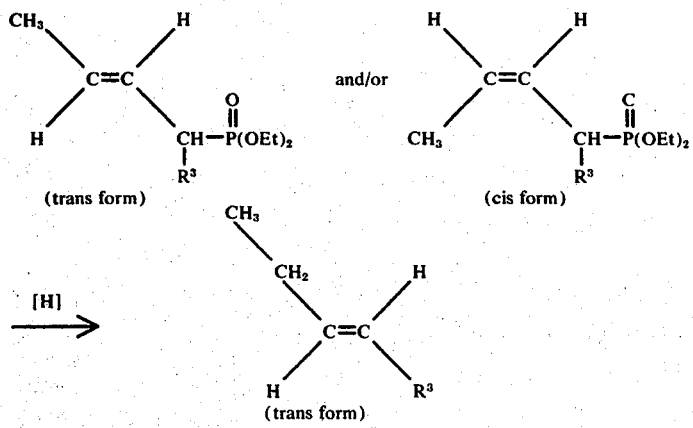

Of the starting 2-alkenylphosphonic acid derivatives of formula (II), those in which R is an alkyl group containing 1 to 4 carbon atoms are most preferably used. $R^1$ and $R^2$ each represent a hydrogen atom, or an akyl or alkenyl group, and they do not represent hydrogen atoms at the same time. Preferred alkyl groups are those containing 1 to 20 carbon atoms, and preferred alkenyl groups are those containing 2 to 20 carbon atoms. $R^3$ is an unsubstituted or substituted alkyl group, preferably an alkyl group containing 1 to 15 carbon atoms, an unsubstituted or substituted alkenyl group, preferably an alkenyl group containing 2 to 15 carbon atoms, or an aralkyl group such as benzyl or phenethyl group. Examples of substituents in the substituted alkyl or alkenyl groups are hydroxyl and carbonyl groups. These substituents can be protected with a protective group generally known in chemical fields to be a group protecting a hydroxyl or carbonyl group, such as an alkoxy, benzyloxy, acetal, silyloxy or tetrahydropyranyloxy group.

The metal hydride used to reduce the starting material of formula (II) includes hydrides of light metals and heavy metals. Typical examples of the light metal hydrides are those containing in Al—H bond, such as lithium aluminum hydride, iso-butyl aluminum hydrides, sodium bis(2-methoxyethoxy) aluminum hydride or aluminum hydrides, and those containing a B—H bond, such as borane or potassium borohydride. Examples of the heavy metal hydride include iron hydride, and copper hydride. These heavy metal hydrides can be formed in situ in the reaction system by mixing the respective metal salts with, for example, lithium aluminum hydride. Aluminum hydride-type compounds are most conveniently used because of their ready availability, ease of handling, and good reactivity. Preferably, the amount of the metal hydride is equivalent to, or in excess of, the starting phosphonic acid derivative.

Conveniently, the reaction is carried out in an inert organic medium that does not participate in the reaction, for example, ether, tetrahydrofuran, benzene, or other hydrocarbon-type solvents with stirring. The reaction temperature is $-20°$ to $+50°$ C., preferably $0°$ to $20°$ C. The reaction proceeds smoothly without the need for any difficult procedure. If the temperature is too high, side-reactions tend to occur.

After the reaction has been completed, the final product can be isolated from the resultant reaction mixture by suitable means such as extraction, washing, and vacuum distillation. The 1,2-disubstituted-olefin so obtained is only of the trans form, as confirmed by its gas chromatogram, NMR spectrum and IR spectrum.

Insect pheromones previously mentioned can be obtained by converting the terminal portion of group $R^3$ of the 1,2-disubstituted-trans-olefin of formula (I) to an ester or aldehyde group. The above olefins can also be used for synthesis of other organic compounds.

The process for preparing the 2-alkenylphosphonic acid derivatives of formula (II) used as starting materials for preparing the above 1,2-disubstituted-trans-olefins will now be described. This process is also a novel process discovered for the first time by the inventors of the present application.

The process for preparing the 2-alkenylphosphonic acid derivatives of formula (II)

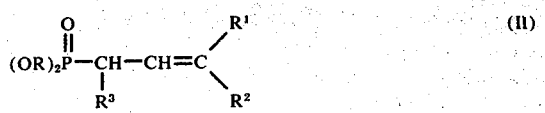

comprises reacting 2-alkenylphosphonic acid esters of formula (III)

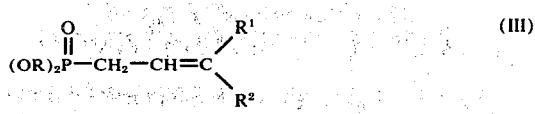

with organic halogen compounds of formula (IV)

$R^3X$ in the presence of strong bases capable of abstracting an acidic hydrogen atom. In the above formulae, R, $R^1$, $R^2$ and $R^3$ are the same as defined above, and X is a halogen atom.

The process of this invention is very characteristic in that, as seen from the formula (II), it affords a derivative in which group $R^3$ is introduced selectively only into the $\alpha$-position. Methods for preparing allylphosphonic acid derivatives of a similar structure have previously been known. For example, E. J. Corey, J. Org. Chem., 34, 3053 (1969) discloses a process in which allylphosphonamide is condensed with a ketone in the presence of a base. However, in these conventional methods, the position on which a particular group is introduced is not selective; i.e. condensation occurs on both $\alpha$- and $\gamma$-positions.

The starting 2-alkenylphosphonic acid ester of formula (III) can be easily obtained, for example, by condensation of a trialkyl phosphite or a sodium dialkyl phosphite with a corresponding halogenated 2-alkenyl halide. The organic halogen compound of formula (IV) as the other starting material may be various unsubstituted or substituted alkyl halides, unsubstituted or substituted alkenyl halides, and aralkyl halides corresponding to the type of the group $R^3$.

This reaction must be carried out in the presence of a strong base capable of abstracting an acidic hydrogen atom. These strong bases are well known in chemical fields, and typical examples include alkylated alkali metals such as butyl lithium, alkali metal hydrides such as sodium hydride, alkali metal amides such as sodium amide, and alkali metal alkoxides such as potassium t-butoxide. All of these compounds are used suitably in the present invention.

Conveniently, the reaction is carried out in an inert organic medium that does not participate in the reaction, for example, ether, tetrahydrofuran, or dimethoxy ethane. The reaction temperature is $-80°$ to $+50°$ C. and the preferred temperature range is $-70°$ to $-20°$ C. If the temperature is too high, side-reactions tend to occur. The reaction proceeds easily when substantially equimolar proportions of the starting compounds of formulae (III) and (IV) are mixed and treated with an equivalent or excessive amount of the strong base under the above mentioned conditions. The final product can be recovered from the resultant reaction mixture by suitable means such as extraction, washing and vacuum distillation.

The following Examples further illustrate the present invention, but are not intended to limit it. A group of Examples A show the production of 2-alkenylphosphonic acid derivative of formula (II) and a group of Examples B, the production of 1,2-disubstituted-trans-olefins of formula (I).

EXAMPLE A-1

1.92 g of diethyl 2-butenephosphonate was placed in 10 ml. of dry tetrahydrofuran, and the solution was cooled to −70° C. in an atmosphere of argon. 7 ml. of n-butyl lithium (as a 15% by weight n-hexane solution) was gradually added, and the mixture was stirred at −70° C. for 1 hour. The reaction mixture was turbid assuming a pale yellow color. When 1.7 g of benzyl chloride was added to this mixture, it became clear. The temperature of the reaction mixture was gradually elevated to room temperature, and it was stirred for an additional 2 hours. The reaction mixture was then diluted with dilute hydrochloric acid, and extracted with ether. The extract was washed with a solution of sodium hydrogen carbonate, washed with water, and dried. The solution was concentrated, and then the residue was distilled at reduced pressure to afford 2.33 g of diethyl 1-benzyl-2-butenephosphonate having a boiling point of 144° C. (0.3 mmHg) in a yield of 93%. The analysis values of the product were as follows:

IR (KBr) 3000, 2500, 1245, 1055, 1025, 965, 745, 695 cm$^{-1}$

NMR(CCl$_4$)Δ1.26 (t. 6H), 1.62 (t. 3H) 2.3 − 3.3 (m. 3H), 4.01 (p. 4H) 5.3 (m. 2H), 7.10(s, 5H)

For C$_{15}$H$_{23}$O$_3$P

Calculated: C 63.82%, H 8.21%. Found: C 63.66%, H 8.29%.

EXAMPLES A-2 to A-11

By the same procedure as in Example A-1, a phosphonic acid ester of the formula

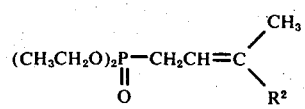

was condensed with an organic halogen compound of the formula

R$^3$X to form a phosphonic acid derivative of the formula

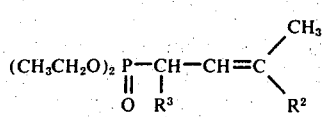

Groups R$^2$, R$^3$ and X, and the yields and properties of the products obtained are shown in Table 1 below. In the table, "THP" stands for tetrahydropyranyl as a protective group.

Table 1

| Examples | R$^2$ | R$^3$ | X | Yield | Properties |
|---|---|---|---|---|---|
| A-2 | H | C$_8$H$_{17}$— | Br | 92 | b.p. 117–188° C/0.04 mmHg |
| A-3 | H | C$_{10}$H$_{17}$—(geranyl group) | Br | 78 | b.p. 142° C/0.08 mmHg |
| A-4 | H | (CH$_3$CH$_2$O)$_2$CHCH$_2$— | Br | 60 | b.p. 102° C/0.08 mmHg |
| A-5 | CH$_3$ | C$_6$H$_5$CH$_2$— | Cl | 87 | Oily substance, IR Spectrum 1600, 1245, 1025, 965 |
| A-6 | CH$_3$ | THPO—CH$_2$ CH=C(CH$_3$)—CH$_2$— | Cl | 65 | Oily substance, IR spectrum 1245, 1020, 960 |
| A-7 | CH$_3$ | C$_8$H$_{17}$— | Br | 94 | b.p. 120° C/0.3 mmHg |
| A-8 | CH$_3$ | C$_{10}$H$_{17}$—(geranyl group) | Br | 91 | b.p. 136° C/0.3 mmHG |
| A-9 | H | THPO(CH$_2$)$_3$— | Br | 90 | Oily substance |
| A-10 | H | THPO(CH$_2$)$_{10}$— | Br | 90 | Oily substance |
| A-11 | H | C$_6$H$_5$CH$_2$CH$_2$— | Br | 85 | b.p. 145° C/0.2 mmHg |

EXAMPLE A-12

The same procedure as in Example A-1 was repeated except that 600 mg of diethyl 6-n-propyl-trans-2,5-nonadienyl-phosphonate and 560 mg of 4-iodo-butanol-tetrahydropyranyl ether were used instead of 1.92 g of the diethyl 2-butene-phosphonate and 1.7 g of the benzyl bromide respectively. There was obtained an oily product in an amount of 745 mg (yield 84%) which had the following structural formula.

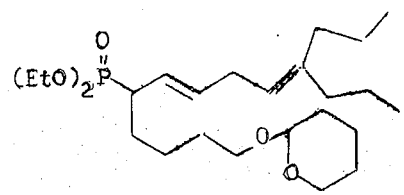

EXAMPLE A-13

The same procedure as in Example A-1 was repeated except that 2,34 g of diethyl 2-heptenephosphonate and 1.42 g of methyl iodide were used instead of 1.92 g of the diethyl 2-butenephosphonate and 1.7 g of the benzyl bromide respectively. Vacuum distillation of the reaction mixture afforded 2.23 g of diethyl 1-methyl-2-heptene-phosphonate having a boiling point of 128° C. (3 mmHg) in a yield of 90%.

EXAMPLE A-14

The same procedure as in Example A-1 was repeated except that 2.18 g of diethyl 2,5-hexadienephosphonate and 1.42g of methyl iodide were used instead of 1.92 g of the diethyl 2-butenephosphonate and 1.7 g of the benzyl bromide respectively. Vacuum distillation of the reaction mixture afforded 2.15 g of diethyl 1-methyl-2,5-hexadienephosphonate having a boiling point of 102° C. (3 mmHg) in yield of 93%.

EXAMPLE B-1

1.4 g (5 millimols) of diethyl 1-benzyl-2-butenephosphonate (a mixture of trans- and cis-forms) was dissolved in 10 ml. of dry ether, and the solution was stirred while being cooled with ice water. To the resulting solution was added 110 mg of lithium aluminum hydride, and the mixture was continued to be stirred. In about 2 hours, the reaction mixture was cooled with ice water, and with stirring, dilute hydrochloric acid was gradually added dropwise to decompose excess lithium aluminum hydride. the reaction mixture was extracted with ether, washed with an aqueous solution of sodium hydrogen carbonate and then with water, and dried. The solution was concentrated, and the residue was distilled at reduced pressure to afford 0.65 g (yield 89%) of 1-phenyl-2-pentene having a boiling point of 88° C. (14 torr). The analysis values of the product were as follows:

IR (KBr cm$^{-1}$) 3050, 3010, 2950, 2900, 1600, 1495, 1445, 965, 750, 690,

Mass ($^m$/e) 146 (M$^+$), 117(B), 115, 104, 91

NMR (CCl$_4$) δ. 0.97 (t, 3H) 2.0 (n, 2H) 3.3(bd, 2H) 5.5(m,2H) 7.20(s, 5H)

EXAMPLES B-2 to B-11

By the same procedure as in Example B-1, a transolefin of the formula

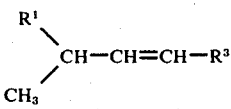

was prepared by treating a phosphonic acid ester of the formula

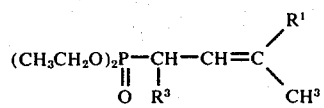

Groups R$^1$ and R$^3$ and the yields and properties of the products are shown in Table 2 below.

Table 2

| Examples | R$^3$ | R$^1$ | Product Yield (%) | Properties |
|---|---|---|---|---|
| B-2 | CH$_3$(CH$_2$)$_7$ | H | 72 | b.p. 96.5 C/16mmHg |
| B-3 | C$_{10}$H$_{17}$— (geranyl group) | H | 82 | b.p. 119° C/15 mmHg |
| B-4 | (CH$_3$CH$_2$O)$_2$CHCH$_2$ | H | 60 | Oily substance |
| B-5 | THP—O—(CH$_2$)$_3$ | H | 75 | Oily substance B.p. of the corresponding alcohol 122° C/12 mmHg |
| B-6 | ph—CH$_2$ | CH$_3$ | 85 | Oily substance IR spectrum (1600.970m$^{-1}$) |
| B-7 | THP—O—CH$_2$CH=C(CH$_3$)(CH$_3$) | CH$_3$ | 89 | Oily substance IR spectrum (1120, 970 m$^{-1}$) |
| B-8 | C$_8$H$_{11}$— | CH$_3$ | 84 | b.p. 94° C/10mmHg |
| B-9 | C$_{10}$H$_{17}$— (geranyl group) | CH$_3$ | 83 | b.p. 117° C/10mmHg |
| B-10 | THPOCH$_2$(CH$_2$)$_9$— | H | 85 | Oily substance |
| B-11 | C$_6$H$_5$CH$_2$CH$_2$— | H | 78 | b.p. 94° C/13mmHg |

EXAMPLE B-12

0.6 g of diethyl 6-propyl-2,5-nonadienylphosphonate was dissolved in 10 ml. of tetrahydrofuran, and an equivalent amount of n-butyl lithium was added at —60° C. in an atmosphere of argon. To this solution was further added 0.56g of 4-butyl iodide-1-tetrahydropyranyl ether. The temperature of the reaction system was gradually elevated to room temperature. The reaction mixture was poured into ice water, and extracted with ether. Concentration of the solvent gave a pale yellow viscous oily substance. The oily product was dissolved in 20 ml. of ether, and reduced with 0.2 g of lithium aluminum hydride to afford 0.5g of 10-propyl-trans-5,9-tridecadiene-1-tetrahydropyranyl ether in a yield of 80%. This ether was treated with a catalytic amount of p-toluenesulfonic acid in methanol to split off the protective group. Thus, there was obtained pure 10-propyl-trans-5,9-tridecadienol in a quantitative yield. The properties of this product were as follows:

Infrared spectrum (KBr): 3250, 2900-2830, 1430, 1050, 950 (cm$^{-1}$)

Nuclear magnetic resonance spectrum (CCl$_4$, δ):
 0.87 (t, 3H), 0.88 (t, 3H), 1.1–1.7 (m, 8H), 1.8–2.2(m, 10H), 2,47(s, 1H), 3.53(m, 2H), 5.1(bt, 1H), 5.4(m, 2H)

EXAMPLE B-13

The same procedure as in Example B-1 was repeated except that 745 mg of a phosphonic acid ester of the following structural formula was used instead of 1.4 g of the diethyl 1-benzyl-2-butenephosphonate.

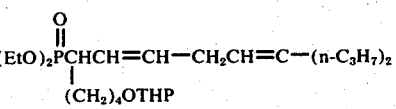

There was obtained 490 mg (yield 90%) of an olefin of the following structural formula

as an oily substance.

EXAMPLE B-14

The same procedure as in Example B-1 was repeated except that 1.24 g of diethyl 1-methyl-2-heptenephosphonate was used instead of 1.4 g of the diethyl 1-benzyl-2-butenephosphonate. There was obtained 0.47 g of trans-2-octene having a boiling point of 125° C. (760 mmHg) in a yield of 84%.

EXAMPLE B-15

The same procedure as in Example B-1 was repeated except that 1.16 g of diethyl 1-methyl-2,5-hexadienylphosphonate was used instead of 1.4 g of the diethyl 1-benzyl-2-butenephosphonate. There was obtained 0.36 g of trans-1,5-heptadiene having a boiling point of 91° C. (760 mmHg) in a yield of 76%.

What we claim is:

1. A process for preparing 1,2-disubstituted-trans-olefins of the following formula

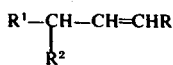
(I)

wherein $R^1$ and $R^2$, independently of each other, represent a hydrogen atom or an alkyl of 1 to 20 carbon atoms or alkenyl of 2 to 20 carbon atoms with the proviso that $R^1$ and $R^2$ do not represent hydrogen atoms at the same time, and $R^3$ represents a hydroxyl substituted alkyl of 1 to 15 carbon atoms, or hydroxyl substituted alkenyl of 2 to 15 carbon atoms, wherein the hydroxyl substituent may be protected with a tetrahydropyranyloxy moiety, which comprises reacting a 2-alkenyl phosphonic acid derivative of the following formula

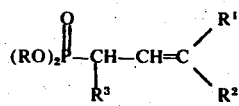
(II)

wherein R is an alkyl containing 1 to 4 carbon atoms, and $R^1$, $R^2$ and $R^3$ are the same as defined above, with a metal hydride containing an Al-H bond selected from the group consisting of lithium aluminum hydride, isobutyl hydride, sodium bis (2-methoxyethoxy) aluminum hydride, and aluminum hydride.

2. The process of claim 1 wherein the reaction is carried out at a temperature of −20° to +50° C.

3. The process of claim 1 wherein the reaction is carried out at a temperature of 0° to 20° C.

4. The process of claim 1 wherein the reaction is carried out in an inert organic medium that does not participate in the reaction.

5. The process according to claim 1 wherein $R^3$ represents a hydroxyl substituted alkyl of 1 to 15 carbon atoms wherein the hydroxyl substituent may be protected with a tetrahydropyranyloxy moiety.

6. The process of claim 1 wherein $R^3$ represents a hydroxyl substituted alkyl of 1 to 15 carbon atoms wherein the hydroxyl substituent is protected with a tetrahydropyranyloxy moiety.

7. The process of claim 1 wherein $R^3$ is THP-O-$(CH_2)_3$ wherein THP represents tetrahydropyranyl moiety.

8. The process of claim 1 wherein $R^3$ is $THPOCH_2(CH_2)$-$_9$ wherein THP represents tetrahydropyranyl moiety.

9. The process of claim 1 wherein said 2-alkenyl phosphonic acid of formula (II) is

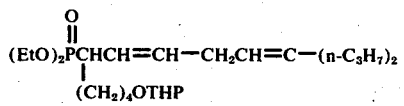

and said 1,2-disubstituted-trans-olefin of formula (I) is

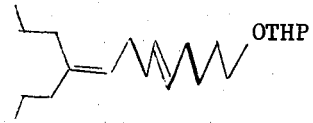

wherein THP represents tetrahydropyranyl moiety.

10. The process of claim 1 wherein said 1,2-disubstituted-trans-olefin of formula (I) is 10-propyl-trans-5,9-tridecadiene-1-tetrahydropyranyl ether.

11. The process of claim 1, wherein said 1,2-disubstituted-trans-olefin of formula (I) is 10-propyl-trans-5,9-tridecadienol.

* * * * *

UNITED STATES PATENT AND TRADEMARK OFFICE
CERTIFICATE OF CORRECTION

PATENT NO. : 3,988,380
DATED : October 26, 1976
INVENTOR(S) : Kiyosi Kondo et al.

It is certified that error appears in the above-identified patent and that said Letters Patent are hereby corrected as shown below:

Claim 1, delete formula (I) in its entirety and insert the following therefor:

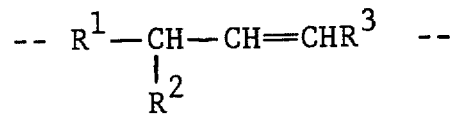

Claim 8, line 2, delete "$THPOCH_2(CH_2)-_9$" and insert:

-- $THPOCH_2(CH_2)\overline{)_9}$ --

Signed and Sealed this

First Day of March 1977

[SEAL]

Attest:

RUTH C. MASON
*Attesting Officer*

C. MARSHALL DANN
*Commissioner of Patents and Trademarks*